United States Patent [19]

Jolly et al.

[11] 4,252,947

[45] Feb. 24, 1981

[54] NOVEL QUINAZOLINONE

[75] Inventors: Jean Jolly, Fontenay-sous-Bois; Primo Rizzi, Villemomble; Jean A. Grandadam, Saint-Maur des Fosses, all of France

[73] Assignee: Roussel Uclaf, Paris, France

[21] Appl. No.: 762,503

[22] Filed: Jan. 26, 1977

[30] Foreign Application Priority Data

Jan. 29, 1976 [FR] France .................. 76 02413

[51] Int. Cl.³ .......................... C07D 401/02
[52] U.S. Cl. .................. 544/287; 424/251; 546/221
[58] Field of Search ............ 260/256.4 Q, 293.52; 424/251; 544/287

[56] References Cited

U.S. PATENT DOCUMENTS

| 2,775,597 | 12/1956 | Baker et al. | 260/293.52 |
| 3,320,124 | 5/1967 | Waletzky et al. | 424/251 |
| 3,336,327 | 8/1967 | Barringer et al. | 260/293.52 |

*Primary Examiner*—Paul M. Coughlan, Jr.
*Attorney, Agent, or Firm*—Hammond & Littell, Weissenberger and Muserlian

[57] ABSTRACT

The novel product, dextrorotary 7-bromo-6-chloro-3-[3-(3-hydroxy-2-piperidyl)-acetonyl]-4(3H)-quinazolinone and its non-toxic, pharmaceutically acceptable acid addition salts having anticoccidiosis activity and its preparation and use.

2 Claims, No Drawings

NOVEL QUINAZOLINONE

STATE OF THE ART

French Pat. No. 1,550,956 describes 7-bromo-6-chloro-3-[3-(3-hydroxy-2-piperidyl)-acetonyl]-4(3H)-quinazolinone in a racemic mixture and a process for its preparation.

OBJECTS OF THE INVENTION

It is an object of the invention to provide novel dextrorotary 7-bromo-6-chloro-3-[3-(3-hydroxy-2-piperidyl)-acetonyl]-quinazolinone and its non-toxic, pharmaceutically acceptable acid addition salts and to a novel process for their preparation and to novel intermediates.

It is another object of the invention to provide novel coccidiostatic compositions and to provide a novel method of combatting coccidiosis in farm animals.

These and other objects and advantages of the invention will become obvious from the following detailed description.

THE INVENTION

The novel products of the invention are selected from the group consisting of dextrorotary 7-bromo-6-chloro-3-[3-(3-hydroxy-2-piperidyl)-acetonyl]-4(3H)-quinazolinone and its non-toxic, pharmaceutically acceptable acid addition salts.

Examples of suitable acids used to form the non-toxic, pharmaceutically acceptable acid addition salts are mineral acids such as hydrochloric acid, hydrobromic acid, sulfuric acid or phosphoric acid or organic carboxylic acids such as acetic acid, benzoic acid, tartaric acid, fumaric acid or malic acid or organic sulfonic acids such as p-toluene sulfonic acid or methane sulfonic acid. The preferred acid addition salt is the hydrobromide salt.

The novel process of the invention for the preparation of dextrorotary 7-bromo-6-chloro-3-[3-(3-hydroxy-2-piperidyl)-acetonyl]-4(3H)-quinazolinone comprises resolving an acid addition salt, preferably the hydrobromide, of dl trans 1-(3-methoxy-2-piperidyl)-2-propanone, separating the dextrorotary isomer and transforming the latter into dextrorotary 7-bromo-6-chloro-3-[3-(3-hydroxy-2-piperidyl)-acetonyl]-4(3H)-quinazolinone by a known method.

The said known procedure comprises reacting trans 1-(3-methoxy-2-piperidyl)-2-propanone hydrobromide with hydrobromic acid as in U.S. Pat. No. 2,775,597 to form the trans 3-bromo-1-(3-methoxy-2-piperidyl)-2-propanone hydrobromide, reacting the latter with allyl chloroformate as indicated in J. Org. Chem., Vol. 20 (1955), p. 118–142 to block the nitrogen atom of the piperidine with allyloxycarbonyl by forming 1-allyloxycarbonyl-2-(ω-bromoacetonyl)-3-methoxypiperidine, condensing the latter with 6-chloro-7-bromo-3,4-dihydro-4-quinazolinone as described in French Pat. No. 1,550,956 to obtain 7-bromo-6-chloro-3-[3-(1-allyloxycarbonyl-3-methoxy-2-piperidyl)-acetonyl]-4(3H)-quinazolinone, subjecting the latter to hydrobromic acid as taught in French Pat. No. 1,550,956 to obtain 7-bromo-6-chloro-3-[3-(3-hydroxy-2-piperidyl)-acetonyl]-4(3H)-quinazolinone hydrobromide and treating the latter with a base to form the corresponding free base which if desired may be salified with a non-toxic, pharmaceutically acceptable acid to form the desired acid addition salt.

The known process may be used to prepare the desired dextrorotary isomer since the optical configuration is not changed during the process. The process is useful for obtaining dextrorotary 7-bromo-6-chloro-3-[3-(3-hydroxy-2-piperidyl)-acetonyl]-4(3H)-quinazolinone from dextrorotary trans (3-methoxy-2-piperidyl)-2-propanone hydrobromide.

In the preferred mode of the process of the invention, the resolution agent is levo 3-hydroxy-7-methoxy-2,3a,4,5-tetrahydro (3H) benz(e)indene-1-carboxylic acid which has the formula

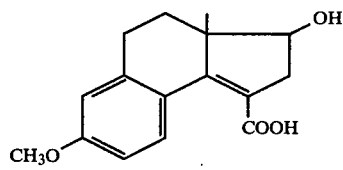

which is a known compound and may be produced by the process described in French Pat. No. 1,205,651. The starting materials for the process are known and may be prepared by the process of J. Org. Chem., Vol. 20 (1955), p. 118–142.

The novel intermediate of the invention is dextrorotary trans (3-methoxy-2-piperidyl)-2-propanone hydrobromide.

The novel coccidiostatic compositions of the invention are comprised of a coccidiostatically effective amount of at least one compound selected from the group consisting of dextrorotary 7-bromo-6-chloro-3-/3-(3-hydroxy-2-piperidyl)-acetonyl/-4(3H)-quinazolinone and its non-toxic, pharmaceutically acceptable acid addition salts and a carrier. The carrier may be those ordinarly used in veterinary medicine or may be an animal feed. The usual dose is 0.5 to 10 ppm of active ingredient of the animal feed. For example, chickens eating 40 to 200 g of feed per day should receive between 20 and 100 ν of active product.

When incorporated into animal feed, the dosage will vary and the animal feed will be varied depending upon the animal being treated. The animal feed contains, for example, 5 to 50 ppm of active ingredient. The nutritive mixture can contain soybean, meat flour, protein hydrolysates, cakes of copra or peanuts, molasses, bran, mineral salts, etc.

When the compositions are in veterinary medicine form, the pharmaceutical carrier may be those excipients ordinarily used for powders, tablets, coated tablets, cachets, capsules, granules, emulsions or syrups. Examples of these are talc, arabic gum, lactose, starch, magnesium stearate, aqueous or non-aqueous emulsions, fatty bodies of animal or vegetable origin, paraffinic derivatives, glycols, preservatives, diverse wetting agents, emulsifiers or dispersants.

The novel method of the invention for combatting coccidiosis in the farm animals comprises administering to farm animals a coccidiostatically effective amount of at least one compound selected from the group consisting of dextrorotary 7-bromo-6-chloro-3-[3-(3-hydroxy-2-piperidyl)-acetonyl]-4(3H)-quinazolinone and its non-toxic, pharmaceutically acceptable acid addition salts. The compositions are preferably orally administered but may be administered in other fashions. The farm animals are especially bovines, sheep and poultry.

Racemic 7-bromo-6-chloro-3-[3-(3-hydroxy-2-piperidyl)-acetonyl]-4-(3H)-quinazolinone and its acid addition salts are known to possess interesting coccidiostatic activity but the dextrorotary compounds of the present invention have been found to be unexpectedly superior thereto. The products of the invention are 3 times greater in their coccidiostatic activity than the corresponding racemic mixture while being only 1.8 times more toxic. One would assume that the toxicity would increase in the same ratio as the coccidiostatic activity and it is surprising that the activity of the claimed optical isomer has a much greater increase in coccidiostatic activity than its toxicity. This may be due to inhibition of the active isomer by the inactive isomer.

In the following examples there are described several preferred embodiments to illustrate the invention. However, it should be understood that the invention is not intended to be limited to the specific embodiments.

EXAMPLE 1 dextrorotary
7-bromo-6-chloro-3-[3-(3-hydroxy-2-piperidyl)-acetonyl]-4(3H)-quinazolinone STEP $A_1$: trans (3-methoxy-2-piperidyl)-2-propanone 250 g of potassium hydroxide were added to a solution of 500 g of trans (3-methoxy-2-piperidyl)-2-propanone hydrobromide in 500 ml of ice water and the mixture was extracted with methylene chloride. The combined organic phases were dried, treated with 25 g of carbon black and evaporated to dryness under reduced pressure to obtain 338.5 g of trans (3-methoxy-2-piperidyl)-2-propanone in the form of an oil which was used as is for the next step.

STEP $A_2$: addition salt of trans
(3-methoxy-2-piperidyl)-2-propanone and levorotory
3-hydroxy-7-methoxy-2,3a,4,5-tetrahydro (3H) benz(e)indene-1-carboxylic acid 150 g of the product of Step $A_1$ were added to a suspension of 240 g of levo 1β-hydroxy-3-carboxy-6-methoxy9aβ-methyl-1,2,3α,8,9,9a-hexahydro-Δ3(3a)-benzo(e)indene in 10.5 liters of anhydrous acetone and the mixture was stirred for 19 hours and was then vacuum filtered. The recovered product was washed and dried to obtain after purfrication 121.7 g of the addition salt of trans (3-methoxy-2-piperidyl)-2-propanone and levo 3-hydroxy-7-methoxy-2,3a,4,5-tetrahydro-(3H)-benz(e)indene-1-carboxylic acid melting about 160° C.

STEP $A_3$: dextrorotary trans
(3-methoxy-2-piperidyl)-2-propanone 50 g of potassium hydroxide pastilles were added at 0° C. to a mixture of 100 g of the product of Step $A_2$ in 200 ml of demineralized water and the mixture was extracted with methylene chloride. The combined extracts were dried and filtered to obtain a clear solution that was concentrated to dryness under reduced pressure to obtain 38.7 g of dextrorotary trans (3-methoxy-2-piperidyl)-2-propanone.

STEP $A_4$: dextrorotary trans
(3-methoxy-2-piperidyl)-2-propanone hydrobromide

A mixture of 38.7 g of the product of Step $A_3$ in 160 ml of an isopropanolic solution titrating 15.5 g of hydrobromic acid per 100 ml was held at 20° C. for 30 minutes and was then vacuum filtered. The recovered product was washed with isopropanol and was dried at 40° C. to obtain 50.4 g of trans (3-methoxy-2-piperidyl)-2-propanone hydrobromide with a melting point of 196° C. and a specific rotation of $[\alpha]_D^{20}=+41°\pm(c=1\%$ in methanol).

STEP B: dextrorotary trans
3-bromo-1-(3-methoxy-2-piperidyl)-2-propanone hydrobromide Using the procedure of U.S. Pat. No. 2,775,597, the product of Step $A_4$ was reacted with a solution of 15% hydrogen bromide in acetic acid for 2 hours at room temperature and the mixture was evaporated to dryness under reduced pressure to obtain dextrorotary trans 3-bromo-1-(3-methoxy-2-piperidyl)-2-propanone hydrobromide melting at 143° C. and having a specific rotation $[\alpha]_D^{20}=+25°$ (c=1% in methanol).

STEP C: levo
1-allyloxycarbonyl-2-(ω-bromoacetonyl)-3-methoxy-piperidine

Using the procedure of J. Organ. Chem., Vol. 20 (1955), p. 118, a solution of the product of Step B in chloroform was cooled on an ice bath and was then neutralized with aqueous sodium bicarbonate. An allyl chloroformate was added to the mixture which was then stirred on the ice bath for 90 minutes. The chloroform phase was washed with N hydrochloric acid, dried over magnesium sulfate and evaporated to dryness under reduced pressure to obtain levo 1-allyloxycarbonyl-2-(ω-bromoacetonyl)-3-methoxy-piperidine with a specific rotation $[\alpha]_D^{20}=-41°$ (c=1% in methanol).

STEP D: levo
7-bromo-6-chloro-3-[3-(1-allyloxycarbonyl-3-methoxy-2-piperidyl)-acetonyl]-4(3H)-quinazolinone Using the procedure of French Pat. No. 1,550,956, a solution of 6-chloro-7-bromo-3,4-dihydro-4-quinazolinone in methanol was added to a solution of the product of Step C in 1.1 N sodium methoxide and the mixture was stirred for 4 hours at room temperature. The solvent was evaporated and the residue was taken up in water. The solution was extracted with chloroform and the organic extracts were dried and evaporated to dryness to obtain levo 7-bromo-6-chloro-3-[3-(1-allyloxycarbonyl-3-methoxy-2-piperidyl)-acetonyl]-4(3H)-quinazolinone with a specific rotation of $[\alpha]_D^{20}=-12°$ (c=1% in methanol) and a melting point of 112° C.

STEP E: dextrorotary
7-bromo-6-chloro-3-[3-(3-hydroxy-2-piperidyl)-acetonyl]-4(3H)-quinazolinone hydrobromide Using the procedure of French Pat. No. 1,550,956, a solution of the product of Step D in an aqueous 48% hydrobromic acid solution was refluxed for an hour and was then evaporated to dryness. The residue in ethanol was refluxed for 30 minutes and the mixture was filtered to obtain dextrorotary 7-bromo-6-chloro-3-[3-(3-hydroxy-2-piperidyl)-acetonyl]-4(3H)-quinazolinone hydrobromide with a specific rotation of $[\alpha]_D^{20}=+6°\pm1°$ (c=1% in a 1—1 methanol-water mixture).

STEP F: dextrorotary
7-bromo-6-chloro-3-[3-(3-hydroxy-2-piperidyl)-acetonyl]-4(3H)-quinazolinone A methanolic potassium hydroxide solution (10 g of KOH/100 ml) was added to a suspension of the product of Step E in methanol and the mixture was stirred for 30 minutes at 20° C. The product was washed with methanol, then with water and was dried to obtain dextrorotary 7-bromo-6-chloro-3-[3-(3-hydroxy-2-piperidyl)-acetonyl]-4(3H)-quinazolinone melting at 205° C. and having a specific rotation of $[\alpha]_D^{20} = +7.5°$ (c=1% in dimethylformamide).

EXAMPLE 2

6 g of the product of Step E of Example 1 were admixed with sufficient calcium carbonate excipient to obtain 1,000 g total weight and the composition was incorporate at a rate of 500 g per metric ton of a complete feed.

COCCIDIOSTATIC ACTIVITY

The coccidiostatic activity of the product of Step E of Example 1 (product A) was studied in comparison with that of a racemic mixture of 7-bromo-6-chloro-3-[3-(3-hydroxy-2-piperidyl)-acetonyl]-4(3H)-quinazolinone (product A-B), 14 day old chicks were weighed and were divided into 3 groups of 13 animals. One group received a feed containing 1 ppm of product A, a second group received a feed containing 3 ppm of product A-B and the 3rd group received just the feed without any additive. The next day, the chicks were infested with Eimeria tenella coccidies and when the chicks were 22 days old, they were weighed as well as the remaining feed. The caecums were removed and the number of caecal lesions were noted. Also noted was (1) the weight of gain (or less) of the chicks as compared to the animals which received product A-B, (2) consumption index which is the amount of feed consumed compared to the weight gain which indice was all the more elevated than the animals which were more sick and (3) the intensity of the lesions on a seal of 1 to 6 were noted. The results are reported in Table I.

TABLE I

|  | 1 ppm of Product A | 3 ppm of Product A-B | Contaminated Controls |
|---|---|---|---|
| weight gain in g | 103.07 (+14.14%) | 90.30 (0%) | 43.07 (−52.30%) |
| consumption index | 1.807 | 2.018 | 3.791 |
| Lesions | 1.65 | 2.38 | 4.84 |

The results of Table I show that product A has a coccidiostatic activity 3 times greater than the racemic product A-B.

ACUTE TOXICITY

The oral acute toxicity was determined for products A and A-B on groups of Swiss female mice by the method of Finney and the results were expressed as $LD_{50}$ (the dose which caused death in 50% of the animals). The $DL_{50}$ for product A was 3.7 mg/kg and for product A-B was 6.8 mg/kg. The acute toxicity of product A is only about 1.8 times greater than product A-B.

Various modifications of the products and processes of the invention may be made without departing from the spirit or scope thereof and it should be understood that the invention is intended to be limited only as defined in the appended claims.

We claim:

1. A process for the preparation of a compound selected from the group consisting of dextrorotary 7-bromo-6-chloro-3-[3-(3-hydroxy-2-piperidyl)-acetonyl]-4-(3H)-quinazolinone and its non-toxic, pharmaceutically acceptable acid addition salts comprising resolving an acid addition salt of dl trans 1-(3-methoxy-2-piperidyl)-2-propane, separating the dextrorotary isomer, reacting the latter with hydrobromic acid to form the trans 3-bromo-1-(3-methoxy-2-piperidyl)-2-propanone hydrobromide, reacting the latter with allyl chloroformate to form 1-allyloxycarbonyl-2-(ω-bromoacetonyl)-3-methoxy-piperidine, condensing the latter with 6-chloro-7-bromo-3,4-dihydro-4-quinazolinone to obtain 7-bromo-6-chloro-3-[3-(1-allyloxycarbonyl-3-methoxy-2-piperidyl)-acetonyl]-4-(3H)-quinazolinone, subjecting the latter to hydrobromic acid to obtain 7-bromo-6-chloro-3-[3-(3-hydroxy-2-piperidyl)-acetonyl]-4-(3H) quinazolinone hydrobromide and treating the latter with a base to form the corresponding free base.

2. The process of claim 1 wherein the resolving agent is levo 3-hydroxy-7-methoxy-2,3a,4,5-tetrahydro (3H) benz(e)indene-1-carboxylic acid.

* * * * *